(12) United States Patent
Hartman

(10) Patent No.: US 8,955,400 B2
(45) Date of Patent: Feb. 17, 2015

(54) AEROSOL SAMPLING DEVICE

(75) Inventor: Mark T. Hartman, Lafayette, IN (US)

(73) Assignee: Caterpillar Inc., Peoria, IL (US)

( * ) Notice: Subject to any disclaimer, the term of this patent is extended or adjusted under 35 U.S.C. 154(b) by 288 days.

(21) Appl. No.: 13/541,971

(22) Filed: Jul. 5, 2012

(65) Prior Publication Data

US 2014/0007708 A1    Jan. 9, 2014

(51) Int. Cl.
*G01N 1/22* (2006.01)
*G01N 1/34* (2006.01)
*G01N 33/28* (2006.01)

(52) U.S. Cl.
CPC .............. *G01N 1/2208* (2013.01); *G01N 33/28* (2013.01)
USPC .................... 73/863.22; 73/31.07; 73/863.81; 123/2

(58) Field of Classification Search
CPC ... G01N 1/2208; G01N 1/34; G01N 33/0011; G01N 33/28; G01N 2001/2226; G01N 2001/2247; G01N 2001/2267
USPC ................. 73/31.07, 863.22, 863.31, 863.81; 123/2
See application file for complete search history.

(56) References Cited

U.S. PATENT DOCUMENTS

| 3,451,895 | A | * | 6/1969 | Webb | G01N 1/22 |
| 3,517,557 | A | * | 6/1970 | Bruder et al. | G01N 1/22 |
| 3,528,279 | A | * | 9/1970 | Lasseur et al. | G01N 1/22 |
| 3,953,182 | A | * | 4/1976 | Roth | 73/863.22 |
| 3,983,743 | A | * | 10/1976 | Olin et al. | G01N 1/2208 |
| 4,274,846 | A | * | 6/1981 | Smith | 73/863.22 |
| 5,049,170 | A | | 9/1991 | Parnoff | |
| 6,431,014 | B1 | * | 8/2002 | Liu et al. | 73/863.22 |
| 7,073,402 | B2 | * | 7/2006 | Trakumas et al. | 73/863.22 |
| 8,783,089 | B2 | * | 7/2014 | Cartier et al. | G01N 1/2208 |
| 2005/0279181 | A1 | * | 12/2005 | Trakumas et al. | 73/863.22 |
| 2007/0044577 | A1 | | 3/2007 | Trakumas et al. | |
| 2011/0088454 | A1 | | 4/2011 | Seeck et al. | |
| 2012/0168634 | A1 | * | 7/2012 | Egen et al. | G01N 1/2208 |
| 2014/0196549 | A1 | * | 7/2014 | Witham | 73/863.22 |

FOREIGN PATENT DOCUMENTS

| GB | 2435934 | | 9/2007 | |
| GB | 2474540 | | 4/2011 | |
| KR | 20040064501 A | * | 7/2004 | B01D 45/08 |
| WO | WO 2009150134 A1 | * | 12/2009 | G01N 1/22 |

OTHER PUBLICATIONS

Oil mist, From Wikipedia, the free encyclopedia, 3 pages, downloaded from http://en.wikipedia.org/wiki/Oil_mist, on Jul. 29, 2014, last modified in Wikipedia on Apr. 19, 2014.*

* cited by examiner

Primary Examiner — Thomas P Noland

(57) ABSTRACT

A sampling device is disclosed. The sampling device includes a labyrinth structure and a sampling tube. The labyrinth structure includes a first baffle plate, a second baffle and a third baffle plate. The second baffle plate in combination with the first baffle plate defines an inlet channel and is configured to receive a portion of oil aerosol containing liquid oil particles. A curved bend is included downstream of the inlet channel and is configured to separate the liquid oil particles from the portion of oil aerosol. The third baffle plate is relatively inclined with respect to the first baffle plate. The third baffle plate in combination with the first baffle plate is configured to drain the separated liquid oil particles. The sampling tube provides the portion of oil aerosol separated of liquid oil particles to a detection device.

19 Claims, 5 Drawing Sheets

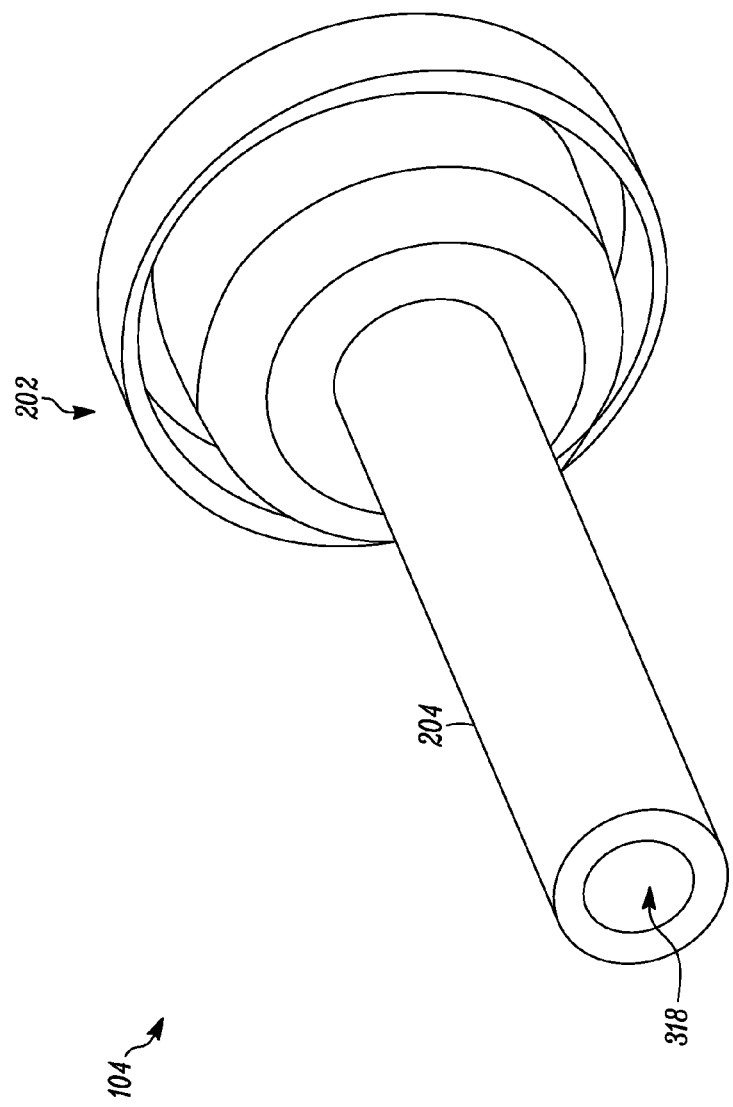

```
500
  ↓
502 ─ RECEIVE A PORTION OF OIL AEROSOL CONTAINING
       SUSPENDED LIQUID OIL PARTICLES
              ↓
504 ─ SEPARATE THE SUSPENDED LIQUID OIL PARTICLES
       FROM THE PORTION OF OIL AEROSOL
              ↓
506 ─ DRAIN THE SEPARATED SUSPENDED LIQUID OIL
       PARTICLES
              ↓
508 ─ RECEIVE THE PORTION OF OIL AEROSOL SEPARATED
       OF THE SUSPENDED LIQUID OIL PARTICLES
              ↓
510 ─ PROVIDE THE PORTION OF OIL AEROSOL SEPARATED
       OF THE SUSPENDED LIQUID OIL PARTICLES
```

AEROSOL SAMPLING DEVICE

TECHNICAL FIELD

The present disclosure relates to sampling devices and more particularly to sampling devices required for aerosol detection systems.

BACKGROUND

A sampler is attached to an engine of a machine in order to extract gas samples and provide the extracted gas samples to a detection system. U.S. Published Application No. 2007/044577 relates to a gas sampler including an impact disc for removing larger particles from a gas flow drawn by a pump and a filter for capturing smaller particles, also positioned in the flow path. The sampler is disassembled and reassembled to remove and replace the impact disc and the filter.

SUMMARY OF THE DISCLOSURE

In one aspect of the present disclosure, a sampling device is provided. The sampling device includes a labyrinth structure and a sampling tube. The labyrinth structure includes a first baffle plate, a second baffle and a third baffle plate. The second baffle plate in combination with the first baffle plate defines an inlet channel and is configured to receive a portion of oil aerosol containing liquid oil particles. A curved bend is included downstream of the inlet channel and is configured to separate the liquid oil particles from the portion of oil aerosol. The third baffle plate is relatively inclined with respect to the first baffle plate. The third baffle plate in combination with the first baffle plate is configured to drain the separated liquid oil particles. The sampling tube provides the portion of oil aerosol separated of liquid oil particles to a detection device.

In another aspect, a method for separating and draining liquid oil particles in a sampling device is provided. The method receives a portion of oil aerosol containing liquid oil particles from a crankcase of an engine. The portion of oil aerosol containing liquid oil particles is received by an inlet channel formed between a first baffle plate and a second baffle plate of a sampling device. The method separates the liquid oil particles from the portion of oil aerosol. The separation occurs near a curved bend present downstream of the inlet channel. Then, the method drains off the separated liquid oil particles from the sampling device through the inlet channel. The separated liquid oil particles slide from a surface of a third baffle plate towards a surface of the first baffle plate to drain out from the inlet channel. The method receives the portion of oil aerosol separated of the liquid oil particles by a sampling tube. Subsequently, the method provides the portion of oil aerosol separated of the liquid oil particles to a detection device.

Other features and aspects of this disclosure will be apparent from the following description and the accompanying drawings.

BRIEF DESCRIPTION OF THE DRAWINGS

FIG. 4 is a solid view of the sampling device; and

FIG. 5 is a process for separating and draining liquid oil particles in a sampling device.

DETAILED DESCRIPTION

Figure 1:
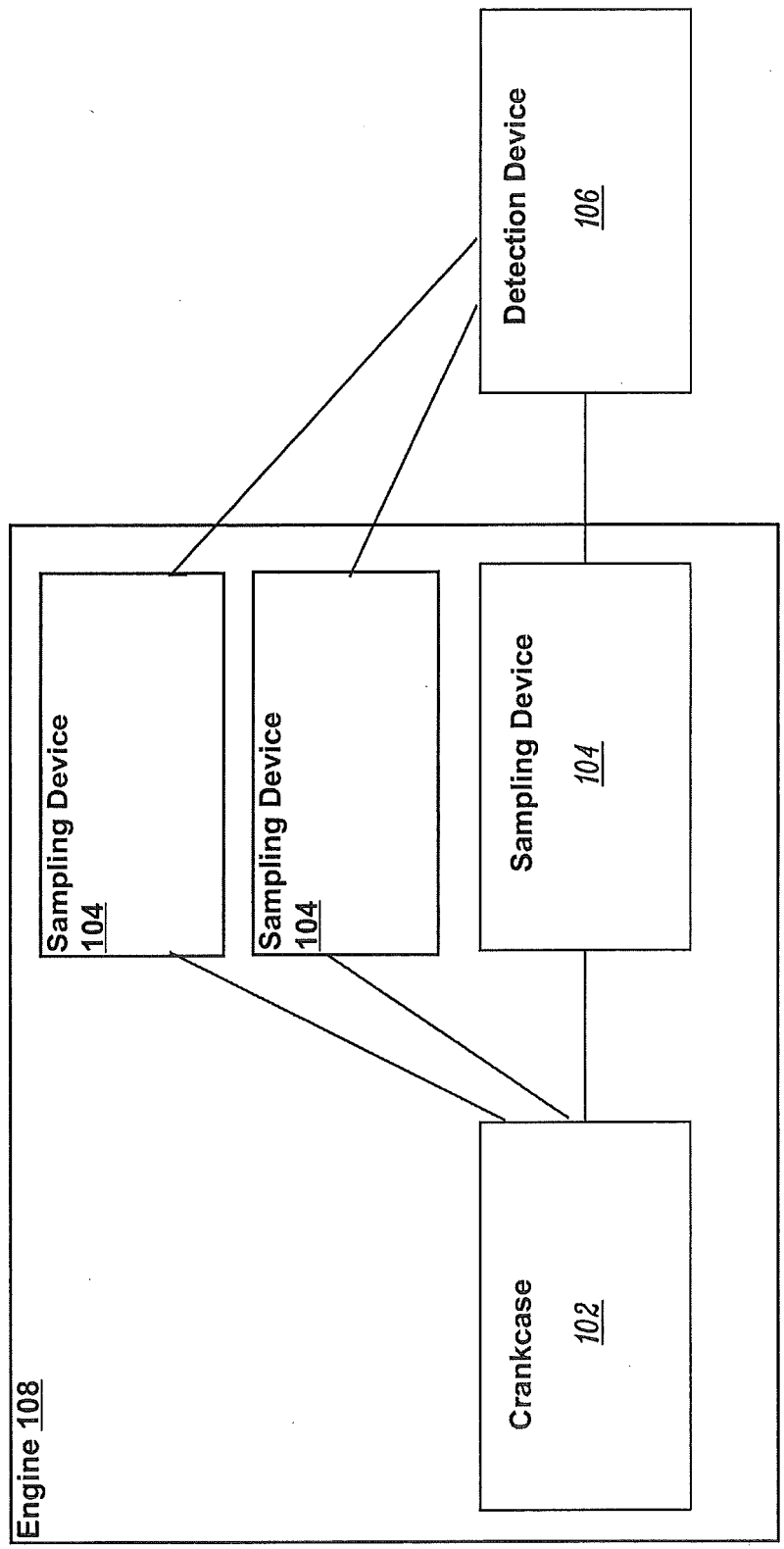
FIG. 1 is a block diagram of a sampling device connected to an engine crankcase.

FIG. 1 illustrates a crankcase 102 of an exemplary engine 108 connected to a sampling device 104, according to one embodiment of the present disclosure. The engine 108 may be an internal combustion, a natural gas engine and the like. The crankcase 102 may include a sampling port to which the sampling device 104 is attached. In one embodiment, a plurality of sampling ports may be present so that a plurality of the sampling devices 104 may be attached to the crankcase 102.

The engine 108 may have moving components that produce oil aerosol in the crankcase 102 of the engine 108. The oil aerosol may contain liquid oil particles which are created in the crankcase 102 of the engine 108 when lubricating oil is splashed by moving and rotating parts of the engine 108.

A detection device 106 may be connected to the crankcase 102 by the sampling device 104. A portion of the oil aerosol containing the liquid oil particles may be supplied to the detection device 106 via the sampling device 104. In one embodiment, the detection device 106 may include an oil mist detector. The oil mist detector is generally used with engines where moving components of the engines may produce oil aerosol inside the crankcase 102. The oil mist detector may be used to detect oil aerosol concentrations indicative of a bearing or a rotating component failure. A high level of oil aerosol concentration may have undesirable effects like machine component shutdown or may even lead to an explosion in the crankcase 102 of the engine 108 in some cases. Hence, in order to avoid these undesirable effects, the oil mist detector may produce an alarm if the oil aerosol concentration reaches beyond a pre-defined limit.

Figure 2:
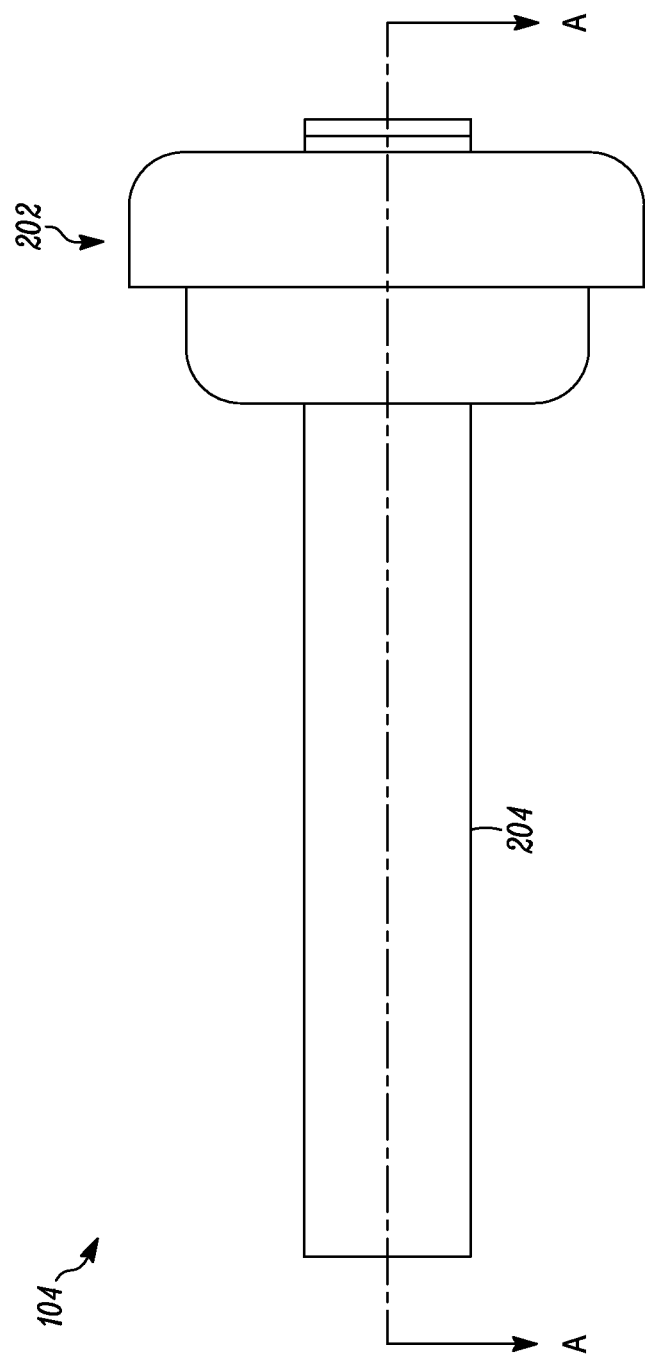
FIG. 2 is a diagrammatic view of the sampling device having a plane AA.
Figure 3:
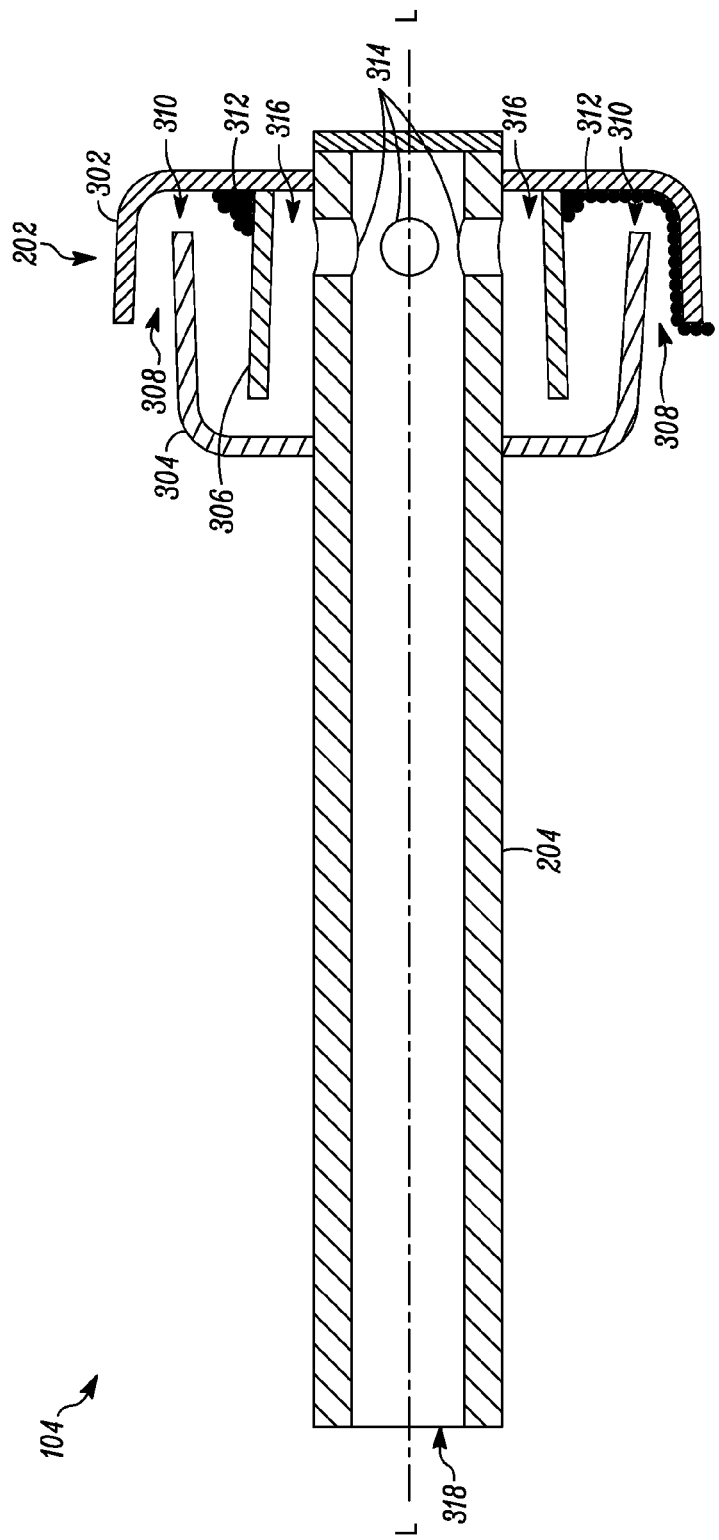
FIG. 3 is a sectional view of the sampling device along the plane AA shown in FIG. 2.

As shown in FIGS. 2 to 4, the sampling device 104 may include a labyrinth structure 202 and a sampling tube 204. The sampling device 104 may be composed of steel. FIG. 2 illustrates a diagrammatic view of the sampling device 104 having a plane AA. The sectional view of the sampling device 104 along the plane AA is shown in FIG. 3. FIG. 4 illustrates a solid view of the sampling device 104.

Referring to FIG. 3, the labyrinth structure 202 may include a first baffle plate 302, a second baffle plate 304, and a third baffle plate 306. The labyrinth structure 202 of the sampling device 104 may be placed inside the crankcase 102 of the engine 108. In one embodiment, the first baffle plate 302 may have a bell shape. As shown in the accompanied figures, the second baffle plate 304 may be partly located within the first baffle plate 302. The second baffle plate 304 may have an inverted bell shape, such that a diameter of the second baffle plate 304 may be less than a diameter of the first baffle plate 302. In another embodiment, outer walls of the second baffle plate 304 may be substantially inclined with respect to the first baffle plate 302.

Further, the second baffle plate 304 in combination with the first baffle plate 302 may define an inlet channel 308. The inlet channel 308 may be configured to receive the portion of the oil aerosol containing the liquid oil particles from the crankcase 102 of the engine 108. The configuration of the second baffle plate 304 of the sampling device 104 within the first baffle plate 302 is such that a curved bend 310 may be present downstream of the inlet channel 308. The liquid oil particles being comparatively heavier than the oil aerosol are separated from the portion of oil aerosol when the received oil aerosol passes over the curved bend 310.

In one embodiment, the third baffle plate 306 may be relatively inclined with respect to the first baffle plate 302. Additionally, the third baffle plate 306 may be placed within the second baffle plate 304 and in contact with the first baffle plate 302. A diameter of the third baffle plate 306 may be lesser than the diameter of the second baffle plate 304.

The separated liquid oil particles 312 may collect on a surface of the third baffle plate 306, as shown in FIG. 3. Moreover, the design and placement of the third baffle plate 306 in the labyrinth structure 202 is such that the third baffle plate 306 in combination with first baffle plate 302 may facilitate in draining of the separated liquid oil particles 312 which are collected on the surface of the third baffle plate 306. It may be understood that the configuration of the labyrinth structure 202 is such that gravity forces the separated liquid oil particles 312 to slide from a surface of the third baffle plate 306 towards a surface of first baffle plate 302 baffle plate and drain out of the sampling device 104 via the inlet channel 308.

As shown in FIGS. 2 to 4, the sampling tube 204 may be present at a center of the sampling device 104. The sampling tube 204 may further include a plurality of holes 314 (see FIG. 3) to receive the portion of oil aerosol separated of liquid oil particles from a channel 316 formed between the third baffle plate 306 and the sampling tube 204.

In one embodiment, a washer may be fitted on the sampling tube 204 ahead of the holes 314 in order to prevent any stranded liquid oil particles from entering into the sampling tube 204. The sampling tube 204 may extend outwards of the crankcase 102 towards the detection device 106. In one embodiment, the sampling tube 204 may be connected to a manifold of the detection device 106 via an opening 318. The sampling tube 204 may provide the portion of the oil aerosol separated of the liquid oil particles from the labyrinth structure 202 of the sampling device 104 to the detection device 106.

Further, in one embodiment, the sampling device 104 may have a substantially horizontal orientation within the crankcase 102 of the engine 108. In another embodiment, the sampling device 104 may have a substantially inclined orientation of, for example, any angle within ±45° about an axis LL of the sampling tube 204, within the crankcase 102.

INDUSTRIAL APPLICABILITY

Detection devices 106 such as oil mist detectors are required to detect the concentration of oil aerosol present in the crankcase 102 of the engine 108. Oil mist detectors make use of optical sensors to detect and measure the density of the oil aerosol received from the crankcase 102. However, the oil aerosol received by the detection device 106 generally contains liquid oil particles. For the proper functioning of the detection device 106 and in order to obtain accurate readings, the liquid oil particles need to be separated from the oil aerosol and provided to the detection device 106.

Typically, a known sampling device is used to separate the liquid oil particles from the oil aerosol and allow the oil aerosol separated of the liquid oil particles to pass through to the detection device 106. However, in the known sampling device, the separated liquid oil particles did not effectively drain out the separated liquid oil particles 312, resulting in the clogging of the known sampling device. The separated liquid oil particles 312 collected in the known sampling device and led to reduction in an effective inlet area causing an increase in the velocity of the oil aerosol inside the known sampling device. The increase in the velocity of the oil aerosol caused a reduction in the ability of the known sampling device to drain from the known sampling device and effectively lead to sealing of the inlet area of the known sampling device. Moreover, some portion of the liquid oil particles may have passed through a plumbing for the detection device 106 and then into the detection device 106 itself.

The sampling device 104, as described above, includes the labyrinth structure 202 so designed such that gravity forces the separated liquid oil particles 312 to drain around the third baffle plate 306 and slide towards the first baffle plate 302 and subsequently fall out of the sampling device 104. The labyrinth structure 202 hence effectively allows the inlet channel 308 of the sampling device 104 to remain unobstructed, thereby allowing free flow of the portion of oil aerosol to the detection device 106.

Also, currently available sampling devices were relatively larger in size, and hence they could not be accommodated in certain engine applications. Contrarily, the sampling device 104 disclosed herein has a smaller size than currently available solutions, allowing the sampling device 104 to be installed in a variety of applications.

FIG. 5 is a flowchart illustrating a method 500 for separating and draining the separated liquid oil particles 312 from the sampling device 104. At step 502, the portion of oil aerosol containing the liquid oil particles may be received from the crankcase 102 of the engine 108 into the labyrinth structure 202 of the sampling device 104. The inlet channel 308 may be formed between the first and second baffle plates 302, 304 and may be configured to receive the portion of oil aerosol containing the liquid oil particles. A person of ordinary skill in the art will appreciate that the detection device 106 to which the sampling device 104 is attached may create a pull or a suction force necessary to cause the portion of oil aerosol present in the crankcase 102 to enter into the inlet channel 308 of the labyrinth structure 202.

Subsequently, at step 504, the liquid oil particles may be separated from the received portion of the oil aerosol. The separation of the liquid oil particles may take place near or at the curved bend 310 present downstream of the inlet channel 308. It may be understood that the design of the inlet channel 308 of the labyrinth structure 202 may cause the heavier liquid oil particles present in the portion of oil aerosol to separate out and collect on the surface of the third baffle plate 306, as shown in FIG. 3.

At step 506, the liquid oil particles 312 separated from the oil aerosol are drained from the sampling device 104. The configuration of the third baffle plate 306 with respect to the first baffle plate 302 of the labyrinth structure may allow the separated liquid oil particles 312 collected on the surface of the third baffle plate 306 to slide from the surface of the third baffle plate 306 towards the surface of the first baffle 302 and subsequently drain out from the inlet channel 308 formed between the first and second baffle plates 302, 304. In one embodiment, the separated liquid oil particles 312 may be allowed to drain back into the crankcase 102 of the engine 108. Moreover, in another embodiment, to facilitate the draining of the separated liquid oil particles 312, the sampling device 104 may itself be oriented at an inclination with respect to the axis LL, within the crankcase 102 of the engine 108.

The portion of oil aerosol separated of the liquid oil particles 312 may continue to flow downstream of the inlet channel 308 into the channel 316 formed between the third baffle plate 306 and the sampling tube 204. At step 508, the portion of the oil aerosol separated of the liquid oil particles 312 may be received by the holes 314 present on the sampling tube 204. In one embodiment, a washer may be fitted on the sampling tube 204 ahead of the holes 314 of the sampling tube 204 to prevent any stranded or excess liquid oil particles in the labyrinth structure 202 from trickling into the sampling tube 204. Subsequently, at step 510 the portion of the oil aerosol separated of the liquid oil particles 312 is provided to the detection device 106 via the opening 318 in the sampling tube 204.

A person of ordinary skill in the art will appreciate that the sampling device 104 is symmetrical and may be mounted at a pre-determined height within the crankcase 102 of the engine 108. It may be understood that parameters related to the sampling device 104 such as length, size, and material used may vary.

While aspects of the present disclosure have been particularly shown and described with reference to the embodiments above, it will be understood by those skilled in the art that various additional embodiments may be contemplated by the modification of the disclosed machines, systems and methods without departing from the spirit and scope of what is disclosed. Such embodiments should be understood to fall within the scope of the present disclosure as determined based upon the claims and any equivalents thereof.

What is claimed is:

1. A sampling device comprising:
   a labyrinth structure including:
      a first baffle plate;
      a second baffle plate partly located within the first baffle plate, the second baffle plate in combination with the first baffle plate defining an inlet channel configured to receive a portion of oil aerosol containing liquid oil particles from a crankcase of an engine, wherein a downstream of the inlet channel includes a curved bend configured to separate the liquid oil particles from the portion of oil aerosol; and
      a third baffle plate relatively inclined with respect to the first baffle plate, wherein the third baffle plate in combination with the first baffle plate is configured to drain the separated liquid oil particles from the inlet channel to the crankcase of the engine; and
   a sampling tube located within the labyrinth structure and extending outwards towards a detection device, the sampling tube configured to provide the portion of oil aerosol separated of liquid oil particles from the labyrinth structure to the detection device.

2. The sampling device of claim 1, wherein the labyrinth structure of the sampling device is attached to a sampling port located within the crankcase of the engine.

3. The sampling device of claim 1, wherein the sampling device has a substantially horizontal orientation within the crankcase of the engine.

4. The sampling device of claim 1, wherein the sampling device has a substantially inclined orientation within the crankcase of the engine.

5. The sampling device of claim 1, wherein the sampling tube is connected to a manifold of the detection device via an opening.

6. The sampling device of claim 1, wherein the detection device is an oil mist detector.

7. The sampling device of claim 1, wherein the sampling tube further includes a plurality of holes configured to receive the portion of oil aerosol separated of liquid oil particles from a channel formed between the third baffle plate and the sampling tube.

8. The sampling device of claim 7, wherein a washer is fitted ahead of the plurality of holes to prevent the separated liquid oil particles from entering into the sampling tube.

9. The sampling device of claim 1, wherein the first baffle plate is bell shaped and the second baffle plate is inverted bell shaped.

10. The sampling device of claim 1, wherein the third baffle plate is in contact with the first baffle plate.

11. The sampling device of claim 1, wherein the sampling device is composed of steel.

12. An engine comprising:
   a crankcase; and
   a sampling device attached to a sampling port, the sampling device including:
      a labyrinth structure including:
         a first baffle plate;
         a second baffle plate partly located within the first baffle plate, the second baffle plate in combination with the first baffle plate defining an inlet channel configured to receive a portion of oil aerosol containing liquid oil particles from a crankcase of an engine, wherein a downstream of the inlet channel includes a curved bend configured to separate the liquid oil particles from the portion of oil aerosol; and
         a third baffle plate relatively inclined with respect to the first baffle plate, wherein the third baffle plate in combination with the first baffle plate is configured to drain the separated liquid oil particles from the inlet channel to the crankcase of the engine; and
      a sampling tube located within the labyrinth structure and extending outwards towards a detection device, the sampling tube configured to provide the portion of oil aerosol separated of liquid oil particles from the labyrinth structure to the detection device.

13. The engine of claim 12 further including a plurality of sampling devices.

14. The engine of claim 12, wherein the sampling device has a substantially horizontal orientation within the crankcase.

15. The engine of claim 12, wherein the sampling device has a substantially inclined orientation within the crankcase.

16. The engine of claim 12, wherein the sampling tube is connected to a manifold of the detection device via an opening.

17. The engine of claim 12, wherein the detection device is an oil mist detector.

18. The engine of claim 12, wherein the sampling tube further includes a plurality of holes configured to receive the portion of oil aerosol separated of liquid oil particles from the third baffle plate.

19. The engine of claim 18, wherein a washer is fitted ahead of the plurality of holes to prevent the separated liquid oil particles from entering into the sampling tube.

* * * * *